United States Patent [19]

Grazioso et al.

[11] Patent Number: 4,616,040
[45] Date of Patent: Oct. 7, 1986

[54] PRODUCTION OF C$_2$-C$_6$ ALIPHATIC ALCOHOLS

[75] Inventors: Michael V. Grazioso, Poughkeepsie, N.Y.; Edwin R. Kerr, deceased, late of Wappinger, N.Y., by Myra L. Kerr, administrator; Richard F. Love, Beacon, N.Y.; David A. Storm, Montvale, N.J.

[73] Assignee: Texaco Inc., White Plains, N.Y.

[21] Appl. No.: 757,408

[22] Filed: Jul. 22, 1985

[51] Int. Cl.$^4$ .............................................. C07C 27/06
[52] U.S. Cl. ..................................... 518/713; 502/305
[58] Field of Search ................................ 518/713, 714

[56] References Cited

FOREIGN PATENT DOCUMENTS 1155463 10/1983 Canada .
660678 7/1929 France .

*Primary Examiner*—Howard T. Mars
*Attorney, Agent, or Firm*—Robert A. Kulason; James J. O'Loughlin

[57] ABSTRACT

A method is provided for preparing a mixture of lower aliphatic alcohols characterized by containing a substantial proportion of aliphatic alcohols having from 2 to 6 carbon atoms by reacting a mixture of carbon monoxide and hydrogen under suitable conditions of temperature and pressure in the presence of a catalyst comprising molybdenum, a metal from the group consisting of cobalt, iron and nickel, and copper, said catalyst being modified by the addition of a promoter from the class consisting of potassium, cesium and rubidium, said promoter being employed at a concentration ranging from about 1.8 to 13.0 micromoles of said alkali per square meter of surface area of said catalyst.

23 Claims, No Drawings

PRODUCTION OF $C_2-C_6$ ALIPHATIC ALCOHOLS

BACKGROUND OF THE INVENTION

1. Field of the Invention

This invention relates to a process for preparing lower aliphatic alcohols. More particularly, this invention relates to the production of a mixture of lower aliphatic alcohols characterized by containing a substantial proportion of alcohols having from 2 to 6 carbon atoms.

Lower aliphatic alcohols have been proposed as fuel extenders or as replacements for gasoline for fueling internal combustion engines. Certain mixtures of lower aliphatic alcohols have the EPA approval for use and are currently being marketed in the United States. The lower aliphatic alcohols can be produced from domestically available non-petroleum sources, and their use in fuels would serve to lessen the dependence of the nation on imported petroleum and petroleum products.

Hydrogen and carbon monoxide, or a synthesis gas mixture of hydrogen and carbon monoxide, can be reacted to form lower aliphatic alcohols. The synthesis gas feed stream can be produced from non-petroleum sources, such as coal, biomass or other hydrocarbonaceous materials. The synthesis gas mixture itself is produced in a partial oxidation reaction of the hydrocarbonaceous material in commercially available processes such as coal gasification.

Numerous catalytic processes have been studied in attempts to provide a viable process for the production of aliphatic alcohols from synthesis gas or from a mixture of hydrogen and carbon monoxide. Heretofore, the emphasis has been primarily directed to the production of methanol. In contrast, the present process is directed to a method for producing an alchol mixture containing a substantial amount of aliphatic alcohols having from 2 to 6 carbon atoms. Under selected reaction conditions, this process is effective for producing a fraction of higher aliphatic alcohols, i.e. an alcohol fraction consisting of $C_2$ to $C_6$ alcohols, which represents the major or predominant alcohol production in this process.

2. Disclosure Statement

U.S. Pat. No. 1,201,850 discloses a method for the production of hydrocarbons and oxygenated compounds of hydrocarbons by passing an oxide of carbon and hydrogen over a heated catalytic agent under a pressure exceeding 5 atmospheres. A number of catalytic materials are disclosed as well as the fact that a basic compound, such as an alkaline metal hydroxide, can be used with the prescribed catalytic agents.

U.S. Pat. No. 1,625,929 discloses a process for producing methanol in which the catalyst contains copper, cobalt and a metallic halide.

U.S. Pat. No. 3,345,427 discloses a dehydrogenation catalyst and process in which the catalyst consists of nickel, molybdenum and alkali metal oxides on an alumina support.

U.S. Pat. No. 4,096,164 discloses a process for reacting hydrogen and carbon monoxide in the presence of a solid catalyst comprising rhodium with molybdenum or tungsten to produce two carbon atom oxygenated hydrocarbons in which ethanol is the major component.

U.S. Pat. No 4,199,522 discloses a Fischer-Tropsch process for producing olefins and this disclosure is incorporated herein by reference.

U.S. Pat. No. 4,235,801 and 4,246,186 disclose the production of alcohols from a mixture of carbon monoxide and hydrogen in the presence of a rhenium catalyst.

U.S. Pat. No. 4,380,589 discloses a Fischer-Tropsch process for producing hydrocarbons with improved selectivity to $C_2-C_4$ olefins by contacting hydrogen and carbon monoxide in the presence of a catalyst. The catalyst disclosed comprises molybdenum, a promoter comprising alkali or alkaline earth metal, and a binder comprising an iron-containing calcium aluminate cement.

EPA 119609 discloses a process for producing alcohols from synthesis gas using a catalyst containing molybdenum with tungsten, rhenium and an alkali metal. This disclosure is incorporated herein by reference. E.P. 79132 discloses a similar process in which the catalyst contains rhenium, molybdenum and potassium.

Co-assigned application Ser. No. 728,636 filed on Apr. 29, 1985 is directed to a process for producing lower aliphatic alcohols from a mixture of carbon monoxide and hydrogen and its disclosure is incorporated herein by reference.

Previous catalytic processes have been notably effective for converting carbon monoxide and hydrogen feedstocks into hydrocarbons or methanol, but none have been particularly effective for providing high yields of a lower aliphatic alcohol mixture characterized by having a substantial or greater weight amount of alcohols having from 2 to 6 carbon atoms as compared to the co-produced methanol.

SUMMARY OF THE INVENTION

It has been discovered that a mixture of carbon monoxide and hydrogen can be reacted to form a mixture of lower aliphatic alcohols containing a substantial amount of aliphatic alcohols having from 2 to 6 carbon atoms. This reaction is conducted by contacting a feed mixture such as synthesis gas with a novel catalyst composition which exhibits good selectivity for the production of $C_2-C_6$ aliphatic alcohols under suitable conditions of temperature and pressure. The effective catalyst composition comprises a mixture of molybdenum, a metal from the group consisting of cobalt, iron and nickel, and copper. This metal catalyst composition is modified by the addition of a critical amount of an alkali metal promoter from the class consisting of potassium, cesium and rubidium in an amount ranging from about 1.8 to 13.0 micromoles of alkali per square meter of surface area of the catalyst thereby forming a promoted or modified catalyst.

DETAILED EMBODIMENTS OF THE INVENTION

In accordance with this invention, a mixture of carbon monoxide and hydrogen as, for example, a synthesis gas mixture of said reactants, is reacted over a catalyst comprising molybdenum, a metal from the group consisting of cobalt, iron and nickel, and copper, which has been modified by the addition of a promoter from the group consisting of potassium, cesium and rubidium, said promoter being employed at a concentration ranging from about 1.8 to 13.0 micromoles of alkali per square meter of surface area of the catalyst. The nature and the concentration of the promoter on the catalyst are critical. Concentrations of promoter outside of the prescribed range result in a sharp reduction in the effectiveness of this process.

In a commonly assigned copending application Ser. No. 728,636 filed on Apr. 29, 1985, it has been shown that the critical concentration range for the alkali promoter is an amount from about 1.8 to 13.0 micromoles of alkali per square meter of surface area of the catalyst. A preferred alkali promoter concentration is from 2.2 to 10.0 micromoles of alkali per square meter of catalyst surface area with the most preferred alkali promoter concentration being from about 2.5 to about 9.0 micromoles of alkali per square meter of catalyst surface area.

The catalyst can be prepared in a number of ways known in the art. In general, the use of a catalyst support or carrier comprising a relatively refractory, porous, adsorptive and high surface area material is preferred. Conventional carriers or supports, such as alumina, silica, titania, magnesia, silica-alumina and boron phosphates, are suitable support materials for preparing the catalyst for this process. The disclosure in U.S. Pat. No. 4,098,683 is illustrative and is incorporated herein by reference.

A preferred method for preparing the catalyst is to impregnate a carrier, such as alumina, with a source of molybdenum generally in the form of a soluble salt, then with a metal from the class of cobalt, nickel and iron, generally also in the form of a soluble salt and finally with copper in the form of a soluble salt. The impregnation of the carrier with the catalyst metals can be done simultaneously or step-wise. The impregnated carrier is dried and then calcined according to known procedures.

It is essential that the catalyst be modified, i.e. treated or impregnated, with an alkali metal promoter from the group of potassium, cesium or rubidium generally in the form of a salt. The treated or modified catalyst is then subjected to reduction with hydrogen gas generally by heating the promoted catalyst at a temperature between about 300° and 500° C. for an extended period, usually 2 to 8 hours.

The catalyst comprises from about 5 to 50 weight percent of molybdenum calculated as molybdenum trioxide, from about 0.3 to 15 weight percent of a metal from the group consisting of cobalt, nickel and iron calculated as the respective oxide CoO, NiO or $Fe_2O_3$ or mixtures thereof, and from about 1.5 to 8 weight percent of copper as copper oxide (CuO), with the balance being the support. A preferred catalyst composition comprises from about 7 to 30 weight percent of molybdenum trioxide, from about 0.5 to 10 weight percent of cobalt, nickel, or iron oxide or a combination thereof and from about 2 to 6 weight percent of copper. Still more preferred is a catalyst comprising from about 7 to 12 weight percent molybdenum, from about 1.5 to 5 weight percent of a metal from the group consisting of cobalt, iron and nickel or a mixture thereof and from about 2.5 to 5 weight percent of copper, all calculated as hereinabove described.

The catalyst should have a surface area of 125 $m^2$/gm (square meters per gram of catalyst) or more. A more effective catalyst will have a surface area from about 150 to 350 $m^2$/gm and the most preferred will have a surface area from about 160 to 300 $m^2$/gm.

Alternatively, a commercially available catalyst comprising molybdenum, one or more of the metals from the class consisting of cobalt, nickel and iron, and copper meeting the foregoing specifications can be impregnated or modified by treatment with the prescribed alkali metal and then reduced under hydrogen and treated as noted above.

The carbon monoxide and hydrogen employed to form the lower aliphatic alcohols in this process can be provided from any available source. One particularly useful source is synthesis gas produced in the gasification of hydrocarbonaceous materials, such as coals and biomass. An effective gasification process is described in U.S. Pat. No. 3,544,291 wherein a hydrocarbonaceous fuel is partially oxidized with a free oxygen-containing gas in a gas generator. In general, the mole ratio of hydrogen to carbon monoxide employed in this process should range from about 0.1 to 50 moles of hydrogen per mole of carbon monoxide with the preferred ratio being from about 0.5 to 20 moles of hydrogen per mole of carbon monoxide.

The reaction conditions for effecting the conversion of the carbon monoxide-hydrogen feed into lower aliphatic alcohols employing the prescribed catalyst of the invention include a reaction temperature ranging from about 240° to about 400° C. with a preferred temperature range being from about 270° to 360° C. and the most preferred temperature being from about 290° to about 350° C. The effective pressure range for this process is from about $3.4 \times 10^6$ Pa (500 psi) to about $2.4 \times 10^7$ Pa (3500 psi). The preferred pressure range is from about $5.1 \times 10^6$ Pa (750 psi) to about $1.7 \times 10^7$ Pa (2500 psi).

The space velocity employed to effect the conversion of carbon monoxide and hydrogen over the prescribed catalyst to the aliphatic alcohols is a vital feature of this process. In general, the space velocity, that is the volume of gas passed through a given volume of catalyst per hour expressed as GHSV($hr^{-1}$), must be at least 1000. A preferred range is from about 5000 to about 50,000. A highly effective process is realized when the space velocity employed ranges from about 10,000 to about 30,000. Under preferred conditions the ratio of weight percent of $C_2$–$C_6$ alcohols to weight percent methanol can exceed 1, and more preferably can be from 1.25 to 2.

The present invention is more fully described in the following Examples. The reactor used for this work was a 1" I.D. type 316 stainless steel tube. 10 cc of the catalyst was diluted with 90 cc of alpha alumina and packed into the reactor. The catalyst was reduced for 4 hours, at 400° C. at a pressure of 1500 psig with a flow of hydrogen gas at 2.5 liters per minute. The catalyst was then cooled to reaction temperature and subjected to a mixture of hydrogen and carbon monoxide in a ratio of 2:1, at a pressure of 1500 psig and a GHSV of 28,000 $hr^{-1}$.

The product emerging from the reactor was sent through a condensor which liquefied the alcohols and water products. The resulting liquid was analyzed by gas chromatography. The non-condensable gas was also analyzed by gas chromatography.

The selectivity to hydrocarbons, methanol, and alcohols containing 2 to 6 carbon atoms is set forth in the table. The alcohol production in grams of alcohol per gram of catalyst per hour is also set forth in the table. Selectivity is defined as the percentage of carbon atoms converted from carbon monoxide to a specified compound or compounds.

EXAMPLE 1

A promoted catalyst was prepared by impregnating a commercially available catalyst comprising cobalt and molybdenum on an alumina carrier first with a solution of copper nitrate, and after calcination with a solution of potassium carbonate. The commercial catalyst was made by Armak catalyst division, Pasadena, Tex. and sold under the name Ketjen KF 124 LD. The copper nitrate solution was made by dissolving 1.2 grams of copper nitrate in 50 cc of distilled water which was then added to 98.8 grams of the catalyst. The impregnated catalyst was then dried and calcined at 450° C. for several hours. After calcination a solution of 5.9 grams of potassium carbonate, in distilled water, was added to 33.0 grams of the calcined catalyst. This was then dried in a nitrogen purged vacuum oven at 135° C. for several hours. The chemical analysis of the catalyst is set forth in the table under Example 1.

EXAMPLE 2

A second promoted catalyst was made as in example 1, however, the catalyst was impregnated with a solution made by dissolving 4.8 grams of copper nitrate in 50 cc of distilled water, which was added to 95.2 grams of the catalyst. After drying and calcination a solution of 5.6 grams of potassium carbonate, dissolved in distilled water, was added to 32 grams of the calcined catalyst. This was then dried in a vacuum oven for several hours. The chemical analysis of the catalyst is set forth in the table under example 2.

EXAMPLE 3

A promoted catalyst was made as in example 1, however, the catalyst was impregnated with a solution made by dissolving 9.5 grams of copper nitrate in 50 cc of distilled water, which was added to 90.5 grams of the catalyst. After drying and calcination a solution of 5.1 grams of potassium carbonate, dissolved in distilled water, was added to 29.0 grams of the calcined catalyst. The catalyst was then dried in a vacuum oven at 135° C. for several hours. The chemical analysis of this catalyst is set forth in the table under example 3.

EXAMPLE 4

A promoted catalyst was made as in example 1, however, the catalyst was impregnated with a solution made by dissolving 18.2 grams of copper nitrate in 60 cc of distilled water, which was added to 81.0 grams of the catalyst. After drying and calcination a solution of 13.1 grams of potassium carbonate, dissolved in distilled water, was added to the calcined catalyst. The catalyst was then dried at 125° C. for several hours. The chemical analysis of this catalyst is set forth in the table under example 4.

This catalyst was tested in a 0.5 liter stainless steel Berty type recirculating gradientless reactor from Autoclave Engineers. 20 cc of catalyst was used. The conditions for the test were the same as those previously described except that the hydrogen flow during reduction was 5 liters per minute instead of 2.5 liters per minute.

EXAMPLE 5

A promoted catalyst was made as in example 1, however, no copper nitrate was added. 30 grams of potassium carbonate, dissolved in 90 cc of distilled water was added to 170 grams of the base catalyst (KF 124 LD). This was then dried at 135° C. for several hours. The chemical analysis of this catalyst is set forth in the table under example 4.

TABLE I

|  | EXAMPLE | | | | |
| --- | --- | --- | --- | --- | --- |
|  | 1 | 2 | 3 | 4 | 5 (Comp.) |
| Catalyst Composition Wt. % | | | | | |
| $MoO_3$ | 9.9 | 9.5 | 9.5 | 8.7 | 9.7 |
| CoO | 3.4 | 3.4 | 3.4 | 3.0 | 3.1 |
| CuO | 0.4 | 1.7 | 3.4 | 6.2 | — |
| $Al_2O_3$ | 78.3 | 77.9 | 75.7 | 73.1 | 78.3 |
| $K_2O$ | 8.0 | 7.5 | 8.0 | 9.0 | 8.9 |
| $H_2/CO$ Ratio | 2.0 | 2.0 | 2.0 | 2.0 | 2.0 |
| Temperature °C. | 343 | 343 | 343 | 343 | 343 |
| GHSV ($HR^{-1}$) | 28,000 | 28,000 | 28,000 | 28,000 | 28,000 |
| Pressure Pa | $1 \times 10^7$ | $1 \times 10^7$ | $1 \times 10^7$ | $1 \times 10^7$ | $1 \times 10^7$ |
| $\frac{\mu\text{-Mole K}}{M^2} =$ | 6.2 | 5.8 | 6.2 | 6.9 | 6.9 |
| Selectivity (%) To: | | | | | |
| $CO_2$ | 48 | 51 | 42 | 48 | 46 |
| $C_1$–$C_6$ Hydrocarbons | 20 | 21 | 21 | 32 | 31 |
| MeOH | 12 | 10 | 14 | 7 | 7 |
| $C_2$–$C_6$ Alcohols | 19 | 17 | 22 | 13 | 17 |
| Alcohol Production (G/G-hr) | 0.24 | 0.35 | 0.50 | 0.42 | 0.27 |
| $\frac{C_2\text{–}C_6 \text{ Alcohols Wt \%}}{\text{MeOH Liquids Wt \%}} =$ | 1.6 | 1.7 | 1.6 | 1.8 | 2.4 |
| $C_2$ + Alc. Prod. (G/G-hr) | 0.15 | 0.22 | 0.30 | 0.27 | 0.19 |

The foregoing examples demonstrate that a process for the production of lower aliphatic alcohols from a mixture of carbon monoxide and hydrogen within the critical parameters for the prescribed catalyst modified or promoted with the specified alkali metal is effective for producing a high yield of $C_2$–$C_6$ aliphatic alcohols in relation to the production of methanol.

What is claimed is:

1. A method for preparing lower aliphatic alcohols characterized by producing a substantial proportion of aliphatic alcohols having from 2 to 6 carbon atoms which comprises reacting carbon monoxide and hydrogen in the presence of a catalyst at a temperature from about 240° to about 400° C., a pressure from about 500 to about 3000 psi and a gas hourly space velocity of at least 1000, said catalyst comprising from about 5 to about 50 weight percent of molybdenum calculated as $MoO_3$, from about 0.3 to about 15 weight percent of a metal selected from the group consisting of cobalt, iron and nickel, calculated as CoO, Fe$_2$O$_3$ or NiO, respectively, and from about 1.5 to 8 weight percent of copper, calculated as CuO, and the balance a support, said catalyst being modified by the addition of an alkali metal promoter from the class consisting of potassium, cesium and rubidium in an amount ranging from about 1.8 to 13.0 micromoles of said alkali metal per square meter of catalyst surface area.

2. A method according to claim 1 in which said catalyst contains from about 2 to 6 weight percent of said copper determined as CuO.

3. A method according to claim 1 in which said catalyst contains from about 2.5 to 5 weight percent of said copper determined as CuO.

4. A method according to claim 1 in which said reaction is conducted at a temperature ranging from about 270° to 360° C.

5. A method according to claim 1 in which said reaction is conducted at a temperature ranging from about 290° to 350° C.

6. A method according to claim 1 in which said alkali metal promoter is potassium employed at a concentration ranging from about 2.2 to 10.0 micromoles of potassium per square meter of catalyst surface area.

7. A method according to claim 6 in which said promoter is employed at a concentration ranging from about 2.5 to 9.0 micromoles.

8. A method according to claim 1 in which said catalyst is modified by the addition of 2.2 to 10.0 micromoles of cesium per square meter of catalyst surface area.

9. A method according to claim 1 in which said catalyst is modified by the addition of 2.2 to 10.0 micromoles of rubidium per square meter of catalyst surface area.

10. A method according to claim 1 in which said support is selected from the class consisting of alumina, silica, titania, magnesia, silica-alumina and boron phosphates.

11. A method according to claim 1 in which said support is alumina and comprises from about 60 to 80 weight percent of said catalyst.

12. A method according to claim 1 in which said gas hourly space velocity ranges from about 5,000 to 50,000.

13. A method according to claim 1 in which the gas hourly space velocity ranges from about 10,000 to about 30,000.

14. A method according to claim 1 in which the molar ratio of hydrogen to carbon monoxide ranges from about 20:1 to 0.5:1.

15. A method according to claim 1 in which said catalyst has a surface area greater than about 125 m$^2$/gm.

16. A method according to claim 1 in which said catalyst has a surface area ranging from about 150 to 350 m$^2$/gm.

17. A method according to claim 1 in which the weight ratio of the aliphatic alcohols having from 2 to 6 carbon atoms to methanol is at least 1.

18. A method according to claim 1 in which the weight ratio of the C$_2$–C$_6$ alcohols to methanol is in the range of 1.25–2:1.

19. A method according to claim 1 in which the metal components of a catalyst are in the free or combined form.

20. A method for preparing lower aliphatic alcohols in which the weight ratio of the C$_2$–C$_6$ alcohols to methanol is greater than 1 which comprises reacting carbon monoxide and hydrogen in the presence of a catalyst at a temperature from about 270° to 360° C., a pressure from about 750 to 2500 psi and a gas hourly space velocity in the range from about 10,000 to 30,000, said catalyst comprising from about 7 to 30 weight percent of molybdenum calculated as MoO$_3$, from about 0.5 to 10 weight percent of a metal or mixture of metals selected from the group consisting of cobalt, iron and nickel calculated as CoO, Fe$_2$O$_3$ or NiO respectively, and from about 2 to 6 weight percent of copper calculated as CuO, and the balance an alumina support, said catalyst being modified by the addition of an alkali metal promoter from the class consisting of potassium, cesium and rubidium in an amount ranging from about 2.2 to 10.0 micromoles of said alkali metal per square meter of catalyst surface area.

21. A method according to claim 20 in which said alumina support comprises from about 60 to 80 weight percent of said catalyst.

22. A method according to claim 20 in which said catalyst comprises from about 7 to 12 weight percent of molybdenum, from about 1.5 to 5 weight percent of a metal from the class consisting of cobalt, iron and nickel, and from about 2.5 to 5 weight percent of copper.

23. A method according to claim 20 in which said reaction is conducted at a temperature ranging from about 290° to 350° C.

* * * * *